US012653352B2

(12) United States Patent
Aidan

(10) Patent No.: US 12,653,352 B2
(45) Date of Patent: Jun. 16, 2026

(54) WATER-RECYCLING PERSONAL CARE DEVICE AND SYSTEM

(71) Applicant: ELC MANAGEMENT LLC, Melville, NY (US)

(72) Inventor: Christopher Aidan, Austin, TX (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 18/958,445

(22) Filed: Nov. 25, 2024

(65) Prior Publication Data

US 2026/0144413 A1     May 28, 2026

(51) Int. Cl.
| | |
|---|---|
| *A47K 7/02* | (2006.01) |
| *A61L 2/10* | (2026.01) |
| *B01D 53/26* | (2006.01) |
| *C02F 1/00* | (2023.01) |
| *C02F 1/72* | (2023.01) |

(52) U.S. Cl.
CPC ...... *A47K 7/02* (2013.01); *A61L 2/10* (2013.01); *B01D 53/26* (2013.01); *C02F 1/002* (2013.01); *C02F 1/72* (2013.01); *A61L 2202/11* (2013.01); *A61L 2202/16* (2013.01); *B01D 2257/80* (2013.01); *B01D 2258/06* (2013.01)

(58) Field of Classification Search
CPC .......... A61M 1/65; A61M 1/774; A61M 1/79; A47K 7/02; A61H 35/008; A61L 2/10
See application file for complete search history.

(56) References Cited

U.S. PATENT DOCUMENTS

| | | | | |
|---|---|---|---|---|
| 9,814,295 | B2 * | 11/2017 | Chiasson | A45D 34/041 |
| 11,744,999 | B2 * | 9/2023 | Ignon | A61M 37/00 |
| | | | | 604/289 |
| 2003/0034459 | A1 * | 2/2003 | Bonin | A61L 2/06 |
| | | | | 250/491.1 |
| 2009/0147505 | A1 * | 6/2009 | Robinett | H02J 7/35 |
| | | | | 362/183 |

* cited by examiner

*Primary Examiner* — David P Angwin
*Assistant Examiner* — Bradley S Oliver
(74) *Attorney, Agent, or Firm* — MARSHALL, GERSTEIN & BORUN LLP

(57) ABSTRACT

A water-recycling personal care device includes a housing, a pad, a dispenser, and a collection system. The housing has a reservoir that is configured to contain a cleaning agent. The pad is removably connected to the housing, and the dispenser is contained within the housing and configured to dispense a quantity of the cleaning agent from the reservoir. The collection system is configured to collect the quantity of the cleaning agent dispensed from the reservoir after use. The personal care device may communicate with an external device to adjust a quality or amount of the quantity of cleaning agent dispensed from the dispenser.

17 Claims, 8 Drawing Sheets

WATER-RECYCLING PERSONAL CARE DEVICE AND SYSTEM

FIELD OF THE DISCLOSURE

The present disclosure generally relates to a personal care devices and systems for cleansing while minimizing water usage and waste production. More specifically, the present disclosure relates to a facial cleansing device and system having a collection system to collect cleaning agent dispensed from the device after use.

BACKGROUND

Traditional cleansing devices often rely on the availability of water and gravity to apply and remove cleansing products effectively. This dependence poses significant challenges in environments where water is scarce, such as arid regions on Earth, or in microgravity conditions, like those encountered in space stations or during space travel. Moreover, conventional cleansing practices contribute to water waste and environmental degradation.

SUMMARY

Examples within the scope of the present disclosure are directed to a water-recycling personal care device and system.

In an example, a water-recycling personal care device includes a housing, a pad, a dispenser, and a collection system. The housing has a reservoir, and the reservoir is configured to contain a cleaning agent. The pad is removably connected to the housing. The dispenser is contained within the housing and configured to dispense a quantity of the cleaning agent from the reservoir. The collection system is configured to collect the quantity of the cleaning agent dispensed from the reservoir after use.

In an approach, the pad may include an absorbent material to absorb the quantity of the cleaning agent.

In an approach, the collection system may include a vacuum pump in fluid communication with the absorbent material of the pad.

In an approach, the collection system may include a filter chamber into which the quantity of the cleaning agent is pumped by the vacuum pump, the filter chamber may include a filter to remove debris from the quantity of the cleaning agent, the filter chamber may be in fluid communication with the reservoir, and the quantity of the cleaning agent may be returned to the reservoir after passing through the filter.

In an approach, the water-recycling personal care device may further include an oxidizing mechanism configured to oxidize the debris.

In an approach, the dispenser may include an aerator, and the cleaning agent may be a foaming cleaning agent that foams in response to aeration by the aerator.

In an approach, a power source may be contained within the housing and a controller may include a non-transitory memory and one or more processors. The controller may be in electrical communication with the power source.

In an approach, a solar panel array may be in electrical communication with the power source.

In an approach, a kinetic energy harvester may be in electrical communication with the power source.

In an approach, a motor may be within the housing, and the motor may be configured to vibrate the pad.

In an approach, a secondary attachment may be configured to removably attach to the housing and may be interchangeable with the pad.

In an approach, the secondary attachment may be at least one of a replacement microfiber pad, an acne treatment head, a diagnostic head, and an LED light head.

In an approach, the pad may include a plurality of layers, a first layer of the plurality of layers comprising an exfoliating surface, a second layer of the plurality of layers comprising an antimicrobial material, and a third layer of the plurality of layers comprising an absorbent material.

In an approach, a hydration system may include a water cavity positioned within the housing, a nozzle connected to the housing, and a pump configured to pump water between the water cavity and the nozzle.

In an approach, the dispenser may include a lock to prevent accidental dispensing during periods of non-use or under conditions of altered gravity.

In an approach, a sensor may be in communication with the controller, and the sensor may be configured to collect sensor data.

In an approach, the sensor may be one of a temperature sensor, a humidity sensor, an air quality sensor, a biometric sensor, and a pressure sensor.

In an approach, a dehumidifier may be configured to collect water from an environment outside the housing and direct the water to the reservoir.

In an approach, a feedback mechanism may be in communication with the controller, and the feedback mechanism may be configured to provide at least one of visual feedback, olfactory feedback, auditory feedback, and haptic feedback.

In an approach, the water-recycling personal care device may further include a temperature control system.

In an approach, the reservoir may be configured to fluidly connect to a plurality of concentrate chambers, each concentrate chamber containing a respective concentrate suitable for use in the cleaning agent.

In an example, a water-recycling personal care system includes a water-recycling personal care device and an external device. The water-recycling personal care device includes a housing, a pad, a dispenser, a collection system, a power source, a personal care controller, and a personal care wireless communication system. The housing has a reservoir, and the reservoir is configured to contain a cleaning agent. The pad is removably connected to the housing. The dispenser is contained within the housing and is configured to dispense a quantity of the cleaning agent from the reservoir. The collection system is configured to collect the quantity of the cleaning agent dispensed from the reservoir after use. The power source is positioned within the housing. The personal care controller includes a non-transitory memory and one or more processors, and the personal care controller is in communication with the power source, the dispenser, and the collection system. The personal care wireless communication system is in communication with the personal care controller. The external device includes a device controller comprising a non-transitory memory and one or more processors, a user interface including an input device in communication with the device controller, and a device wireless communication system in communication with the device controller and the personal care wireless communication system. The non-transitory memory of the personal care controller stores instructions that, when executed by the one or more processors of the personal care controller, cause the personal care controller to adjust a quality or amount of the quantity of cleaning agent dispensed from the dispenser.

In an approach, the personal care controller may adjust the quality or amount of the quantity of cleaning agent dispensed from the dispenser in response to user input provided at the input device.

In an approach, the water-recycling personal care device may include includes a speaker in communication with the personal care controller, and the personal care controller stores instructions that, when executed by the one or more processors of the personal care controller, cause the speaker to produce an audible signal.

In an approach, the water-recycling personal care device may include a sensor configured to collect sensor data, and the non-transitory memory of the personal care controller stores instructions that, when executed by the one or more processors of the personal care controller, adjusts operation of the water-recycling personal care device in response to the sensor data.

In an approach, adjusting operation of the water-recycling personal care device in response to the sensor data may include at least one of changing the quantity of the cleaning agent dispensed from the dispenser, changing a vibration of the water-recycling personal care device, changing a formulation of the cleaning agent, and changing a vacuum level of the collection system.

In an approach, the water-recycling personal care device may include a motor configured to generate vibrations, and changing the vibration of the water-recycling personal care device may include at least one of turning on the motor, turning off the motor, and adjusting a speed of the motor.

In an approach, the water-recycling personal care device may include a plurality of concentrate chambers, each concentrate chamber of the plurality of concentrate chambers configured to fluidly connect with the reservoir and may further include a respective concentrate suitable for use in the cleaning agent. Changing a formulation of the cleaning agent may include fluidly connecting at least one of the plurality of concentrate chambers to the reservoir to add the respective concentrate of each of the at least one of the plurality of concentrate chambers to the cleaning agent.

In an approach, the collection system may include a vacuum pump in fluid communication with the pad, and changing a vacuum level of the collection system may include adjusting the vacuum level generated by the vacuum pump.

In an approach, the water-recycling personal care device may include a sensor configured to collect sensor data. At least one of the non-transitory memory of the personal care controller and the non-transitory memory of the device controller may store instructions that, when executed by the one or more processors of the personal care controller or the one or more processors of the device controller, stores the sensor data as stored sensor data.

In an approach, at least one of the non-transitory memory of the personal care controller and the non-transitory memory of the device controller may store instructions that, when executed by the one or more processors of the personal care controller or the one or more processors of the device controller, analyzes the stored sensor data and provides personal care recommendations.

In an approach, the personal care recommendations may include at least one of recommending an attachment for the water-recycling personal care device, recommending an adjustment to the quality or amount of the quantity of cleaning agent dispensed, recommending an adjustment to a formulation of the cleaning agent dispensed, recommending an application technique, and recommending an application time.

In an approach, the non-transitory memory of the device controller may store instructions that, when executed by the one or more processors of the device controller, display the personal care recommendations on the user interface.

In an approach, the non-transitory memory of the device controller may store instructions that, when executed by the one or more processors of the device controller, displays input options on the user interface, solicits selection of one or more of the input options by the input device, and communicates the selected one or more of the input options to the personal care controller via the device wireless communication system and personal care wireless communication system. The non-transitory memory of the personal care controller may store instructions that, when executed by the one or more processors of the personal care controller, adjust operation of the water-recycling personal care device in response to the selected one or more of the input options.

In an approach, adjusting the operation of the water-recycling personal care device in response to the selected one or more of the input options may include facilitating replacement of the pad with an attachment, adjusting the quality or amount of the quantity of cleaning agent dispensed, and adjusting a formulation of the cleaning agent dispensed.

In an approach, the water-recycling personal care device may include a feedback mechanism, and at least one of the non-transitory memory of the personal care controller and the non-transitory memory of the device controller may store instructions that, when executed by the one or more processors of the personal care controller or the one or more processors of the device controller, activate the feedback mechanism when a threshold setting has been met.

In an approach, the threshold setting may be one of a period of time expiring and sensor data exceeding a preset sensor threshold.

In an approach, the water-recycling personal care device may include a light on the housing, and the non-transitory memory of the personal care controller may store instructions that, when executed by the one or more processors of the personal care controller, at least one of turns on, turns off, or changes a color of the light in response to a component status.

In an approach, the component status may be one of a use time of the pad, a fill level of the reservoir, a level of power of the power source, and a filter efficacy of the collection system.

In an approach, the water-recycling personal care system may further include a case including a receptacle for storing the water-recycling personal care device. A UV light may be within the case for sanitizing the water-recycling personal care device.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various examples. Also, common but well-understood elements that are useful or necessary in a commercially feasible examples are often not depicted to facilitate a less obstructed view of these various examples. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

BRIEF DESCRIPTION OF THE DRAWINGS

The figures described below depict various aspects of the system and methods disclosed herein. It should be understood that each figure depicts an arrangement of a particular aspect of the disclosed system and methods, and that each of the figures is intended to accord with a possible arrangement thereof.

There are shown in the drawings arrangements which are presently discussed, it being understood, however, that the present embodiments are not limited to the precise arrangements and instrumentalities shown, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various examples. Also, common but well-understood elements that are useful or necessary in a commercially feasible examples are often not depicted to facilitate a less obstructed view of these various examples. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various approaches, a water-recycling personal care device is provided to dispense and remove cleanser without a need for running water or gravity. The water-recycling personal care device can dispense a precise amount of cleanser per application to minimize waste. A collection system can remove the applied cleanser and reuse at least some components of the removed cleanser for future cleansing activity, thereby conserving water. The water-recycling personal care device can be used with an external device to leverage smart technology to offer personalized skincare solutions and maintain user-friendliness and accessibility across diverse user populations and conditions.

Figure 1:
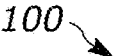
FIG. 1 illustrates a perspective view of a water-recycling personal care device system including a water-recycling personal care device and an external device prior to use of the water-recycling personal care device.
Figure 1:
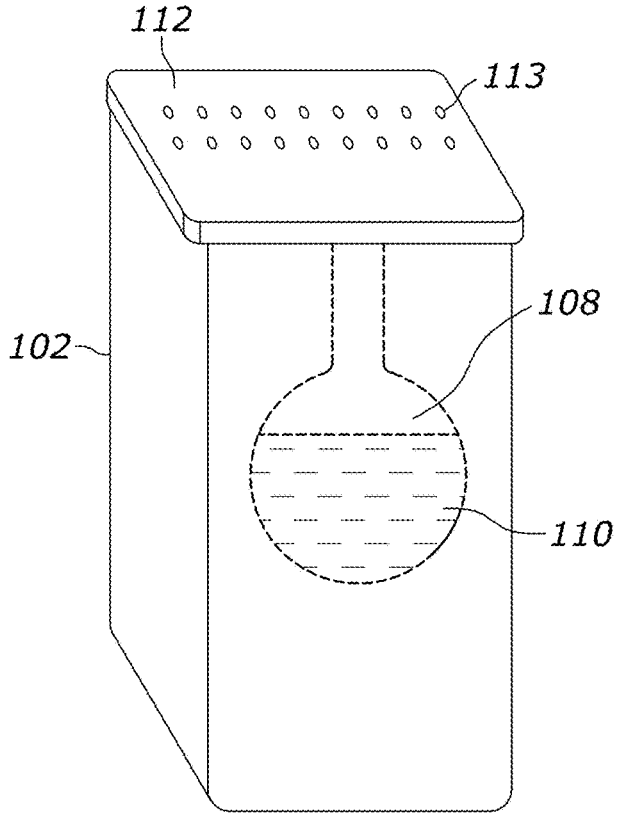
Figure 1:
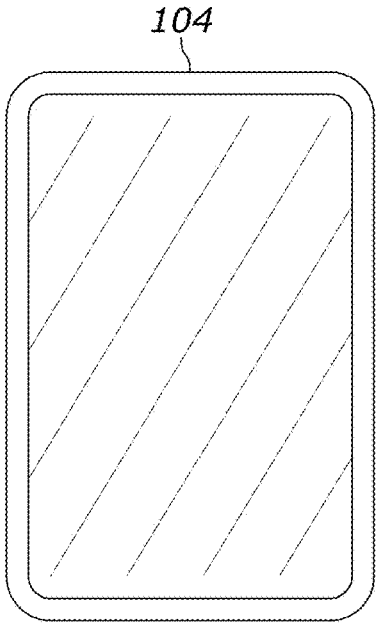

FIG. 1 shows a perspective view of a water-recycling personal care system 100 including a water-recycling personal care device 102 and an external device 104. The water-recycling personal care device 102 includes a housing 106 having a reservoir 108. In the arrangement shown, the housing 106 is ergonomically shaped to be held by a user during use of the device, such as during cleansing of the user's face. In other arrangements, the housing 106 may be arranged to enable hands-free use by, for example, being clipped or otherwise connected to a larger structure, such as a vanity. The reservoir 108 is configured to contain a cleaning agent 110, such as a facial cleanser, which can be dispensed from the water-recycling personal care device 102 onto, for example, a user's hands or face. A pad 112 is removably connected to the housing 106 for use during the cleansing process (e.g., to exfoliate and spread the cleaning agent 110) and to facilitate collection of the cleaning agent 110 after use. The pad 112 may be, for example, a microfiber pad. The pad 112 may be provided with perforations 113 or small holes to facilitate dispensing and collection of cleaning agent 110.

In the arrangement shown, the external device 104 is a smartphone. In other arrangements, the external device may be, for example, be a computer, a smart TV, a tablet, a smartwatch, a wearable device, or another type of external device. The external device 104 is in communication with the water-recycling personal care device 102 and includes a user interface 114 including an input device 116. A user can provide instructions or make selections, as discussed further below, regarding the operation of the water-recycling personal care device 102 using the input device 116 of the user interface 114. A user can adjust a quality or amount of the quantity of cleaning agent dispensed from the dispenser in response to user input provided at the input device 116 by, for example, increasing or decreasing the quantity of cleaning agent, changing the formulation of the quantity of cleaning agent, or changing the aeration level during dispensing.

Figure 2:
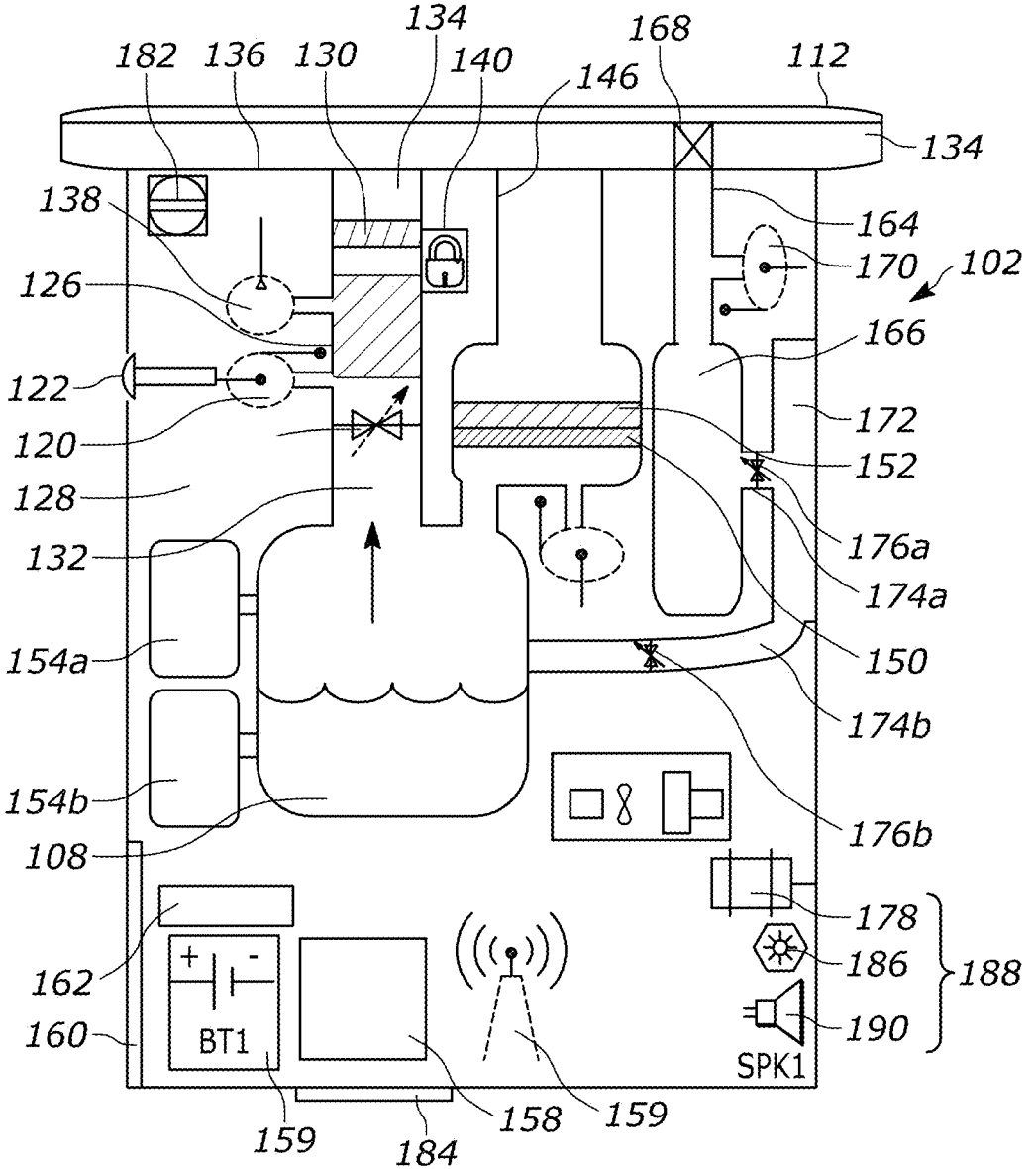
FIG. 2 illustrates a cross-sectional view of the water-recycling personal care device of FIG. 1 during dispensing of a cleaning agent.

FIG. 2 illustrates a cross-sectional view of the water-recycling personal care device 102 during dispensing of a cleaning agent 110. As shown, a dispenser 118 is contained within the housing 106 and is configured to dispense a quantity of the cleaning agent 110 from the reservoir 108. In the arrangement shown, the dispenser 118 includes a vacuum pump 120 having an actuation button 122, a pumping chamber 126 having a one-way valve 128 and a seal 130, a first flow path 132 between the reservoir 108 and the pumping chamber 126, a second flow path 134 between the pumping chamber 126 and a surface 136 of the housing, and an aerator 138 in fluid communication with the pumping chamber 126. The vacuum pump 120 may be a manual vacuum pump that includes a piston and spring assembly.

In use, the user pushes the actuation button 122 to generate a vacuum using the vacuum pump 120. The vacuum pump 120 may be a manual vacuum pump integrated with the actuation button 122 (including, for example, a piston and spring design) or may be an electromechanical vacuum pump 120 as illustrated schematically in FIG. 2. At this stage, the seal 130 is closed to so that, in response to the vacuum formed in the pumping chamber 126, a quantity of cleaning agent 110 moves from the reservoir 108 and through the first flow path 132 and the one-way valve 128 to the pumping chamber 126. The vacuum pump 120 then ceases to generate a vacuum and the seal 130 is opened. The aerator 138 then begins to introduce air into the quantity of cleaning agent 110 in the pumping chamber 126. In some cases, the aerator 138 may act as an air compressor that compresses ambient air into a high-pressure stream of air delivered to the pumping chamber 126. The cleaning agent 110 includes a foaming agent, such as sodium laryl sulfate (SLS), and the introduction of air by the aerator 138 causes the quantity of cleaning agent 110 in the pumping chamber 126 to foam. The foaming causes the quantity of cleaning agent 110 to increase in volume and move through the second flow path 134 to the surface 136, where it can be used for cleansing. The dispenser 118 may include a lock 140, for example between seal 130 and second flow path 134, to prevent accidental dispensing during periods of non-use or under conditions of altered gravity.

Figure 3:
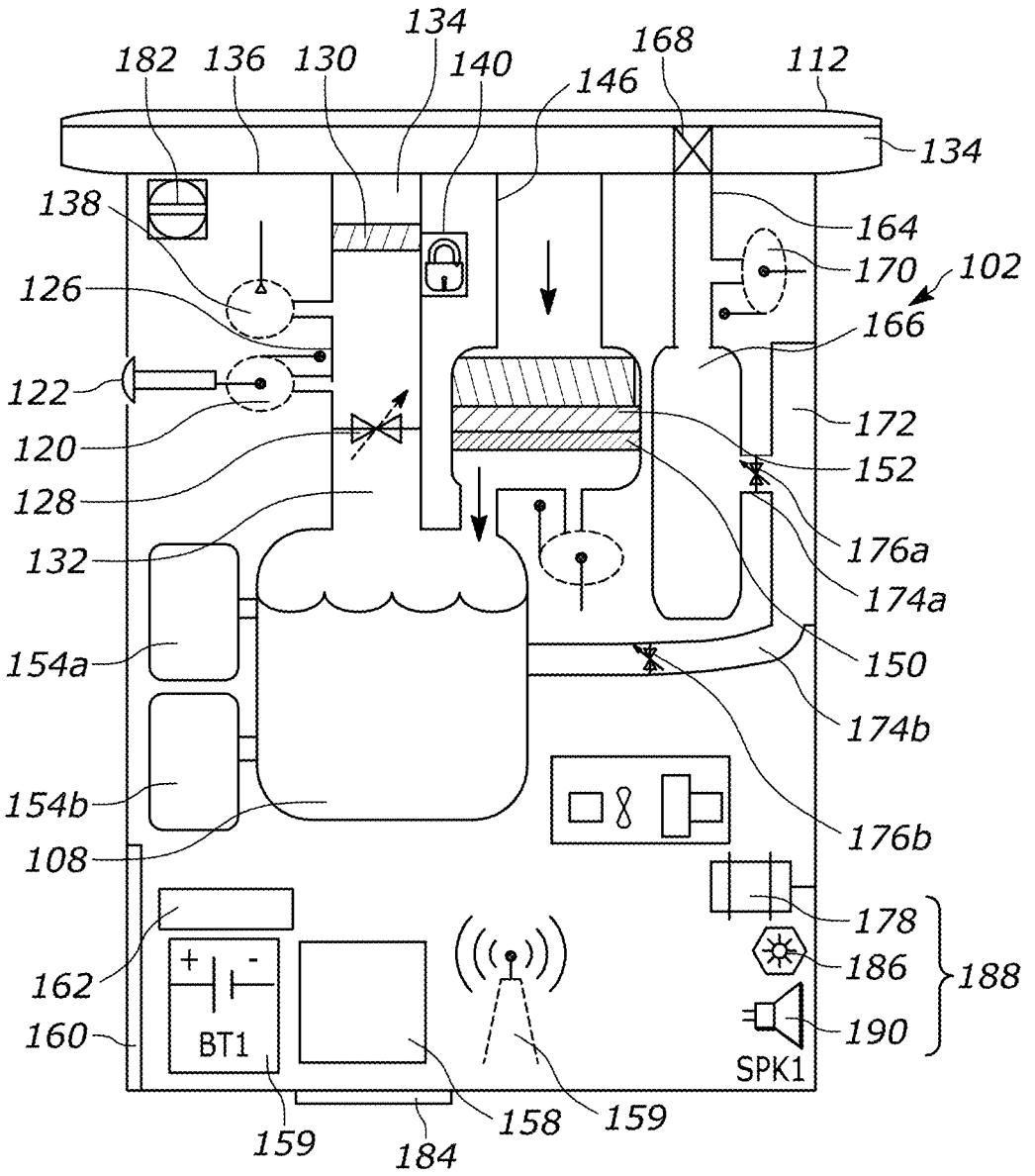
FIG. 3 illustrates a cross-sectional view of the water-recycling personal care device of FIGS. 1 and 2 during collection of the cleaning agent by the collection system.

As shown in FIG. 3, the pad 112 includes an absorbent material 124 to absorb the quantity of the cleaning agent 110 dispensed by the dispenser 118. The water-recycling personal care device 102 has a collection system 142 in fluid communication with the absorbent material 124 of the pad 112. Specifically, the collection system 142 includes a vacuum pump 144 in fluid communication with the absorbent material of the pad 112. In some arrangements, the vacuum pump 144 may be the same as vacuum pump 120 used for the dispenser 118. The collection system 142 includes a return pathway 146 through which used cleaning agent 110 is pumped to a filter chamber 148. The filter chamber 148 includes a filter 150 to remove debris from the used quantity of the cleaning agent 110. An oxidizing mechanism 152 [DETAILS?] may be provided on or near the filter 150 to oxidize the debris. After the cleaning agent 110 has passed through the filter 150, the cleaning agent 110 is returned to the reservoir 108 for further use.

The reservoir 108 is further configured to connect to a plurality of concentrate chambers 154 (e.g., 154a, 154b). The concentrate chambers 154a and 154b each contain a respective concentrate suitable for use in the cleaning agent 110. For example, a first concentrate chamber 154a may contain a first concentrate (such as a surfactant to help remove dirt, oil, and impurities from the skin) and the second concentrate chamber 154b may contain a second concentrate (such as an exfoliant, pH adjuster, or a fragrance).

Additional concentrate chambers 154 may be provided. For example, all potential components of the cleaning agent 110 may be provided, each having its own concentrate chamber 154. Concentrate from a given concentrate chamber 154 may be added to the reservoir 108 to ensure that the cleaning agent 110 has a desired formulation. In particular, concentrates may be added to replace materials that are lost either by being absorbed by user during the cleansing process or by filtering of debris by filter 150. Further, as described further below, the formulation of the cleaning agent 110 may be adjusted to include different levels of the concentrates in chambers 154 in response to certain environmental or skin conditions or as a result of a user's preferences. For example, some users may prefer to have their cleaning agent 110 include a fragrance while others would prefer it to be fragrance-free.

The water-recycling personal care device 102 in FIGS. 2 and 3 also includes a power source 156 positioned within the housing 106, a personal care controller 158 in communication with the power source 156, and a personal care wireless communication system 159 in communication with the personal care controller 158 and configured to communicate with, for example, external device 104. The power source 156 may be, for example, a battery. In some arrangements, the power source 156 may be in communication with a solar panel array 160 or a kinetic energy harvester 162 to receive and store energy from the sun or from movement of the water-recycling personal care device 102. For example, the kinetic energy harvester 162 may include piezoelectric materials that generate an electrical charge when mechanically stressed, may include a magnet that moves relative to a coil to induce an electrical current, or may operate using electrostatic induction where capacitance varies between plates as they move relative to each other.

FIGS. 2 and 3 also illustrate other optional features of the water-recycling personal care device 102. For example, in the arrangement shown, the water-recycling personal care device 102 further includes a hydration system 164. The hydration system 164 includes a water cavity 166 positioned within the housing 106, a nozzle 168 fluidly connected to the housing 106, and a hydration pump 170 configured to pump water between the water cavity 166 and the nozzle 168. The hydration system 164 may be useful to spray a small amount of water for cleansing the face after application of the cleaning agent 110, and the water can be recovered by the collection system 142. Some water is naturally lost during the cleansing process due to evaporation and absorption, so water from the hydration system 164 that is collected by the collection system 142 can be used in the cleaning agent 110 after passing through filter 150 to replace the evaporated or absorbed water. In the arrangement shown, the water-recycling personal care device 102 further includes a dehumidifier 172 to collect moisture from the air for use as water in the water-recycling personal care device 102. In the arrangement shown, the dehumidifier 172 is configured to deliver collected water to either the reservoir 108 or the water cavity 166 via, respectively, passage 174a and passage 174b. Valves 176a and 176b in, respectively, passage 174a and passage 174b control where water collected by the dehumidifier 172 is delivered.

The water-recycling personal care device 102 shown in FIGS. 2 and 3 includes a motor 178 to vibrate the pad 112. In this way, the pad 112 can exfoliate a user's face. As described with respect to FIG. 5 below, secondary attachments 180 may also be provided, such as heads for acne or deep hydration treatments, and the skincare routines enabled by the secondary attachments 180 may also benefit from being vibrated by the motor 178.

Although the pad 112 does not need to be attached to power source 156, some secondary attachments 180 (such as light treatment heads) need a connection to the power source 156 so an outlet 182 for connecting a secondary attachment 180 to the power source 156 is depicted in FIGS. 2 and 3.

The water-recycling personal care device 102 shown in FIGS. 2 and 3 also includes at least one sensor 184 in communication with the personal care controller 158 and the power source 156. In the arrangement shown, the sensor 184 is positioned on the housing 106 to collect sensor data regarding the environment in which the water-recycling personal are device 102 is being used. In other arrangements, more than one sensor 184 may be used in the water-recycling personal care device, and the sensor data collected may relate to internal conditions or operations of the water-recycling personal care device 102 as opposed to environmental conditions outside the water-recycling personal care device. A sensor 184 may be a temperature sensor, a humidity sensor, an air quality sensor, a biometric sensor, a pressure sensor, or any other known type of sensor.

The water-recycling personal care device 102 depicted in FIGS. 2 and 3 includes features that can be used in conjunction or response to sensor data from sensor 184 or independently. For example, a plurality of LED lights 186 may be provided on the housing 106 and in communication with the power source 156 and the personal care controller 158. The LED lights 186 may be operated independently to turn on or off in response to user input. Alternately, the LED lights 186 may be operated as part of a feedback mechanism 188. The feedback mechanism 188 is in communication with the personal care controller 158 and the sensor(s) 184 and is configured to provide at least one of visual feedback, olfactory feedback, auditory feedback, and haptic feedback. For example, the LED lights 186 may be activated in response to sensor data from a sensor 184 as the feedback mechanism 188. For example, the sensor 184 may be a light sensor that provides sensor data indicating how much light is present in the environment around the water-recycling personal care device 102, and the LED lights 186 may turn on when the sensed light is below a certain level. Alternately, or in addition, the water-recycling personal are device 102 includes a speaker 190 in communication with the personal care controller 158 and the sensor(s) 184 and may function as the feedback mechanism 188 to provide auditory feedback. The motor 178 may function as the feedback mechanism 188 to provide haptic feedback by, for example, vibrating the housing 106. Concentrates in the concentrate chambers 154 may function as the feedback mechanism 188 to provide olfactory feedback by, for example, releasing a fragrance in response to sensor data.

As shown in FIGS. 2 and 3, the water-recycling personal care device 102 further includes a temperature control system 192. The temperature control system includes a fan 194 and a heater 196 and can be used in conjunction with a sensor 184 that is a temperature sensor configured to collect sensor data on the temperature of the environment or select components the water-recycling personal care device 102. The fan 194 can be turned on by the personal care controller 158 when temperature data indicates that the environment or select components (e.g., the cleaning agent 110 in the reservoir 108) are getting too cold for optimal operation of the water-recycling personal care device 102. Similarly, the heater 196 can be turned on when the sensor data indicates that the environment or select components (e.g., the motor 178 or vacuum pump 120) are getting too hot for optimal operation of the water-recycling personal care device 102. Although shown schematically in FIGS. 2 and 3, the fan 194 and the heater 196 may be positioned in optimal locations, such as in or near select components, to best distribute heat.

Figures 4, 4A, 4B:
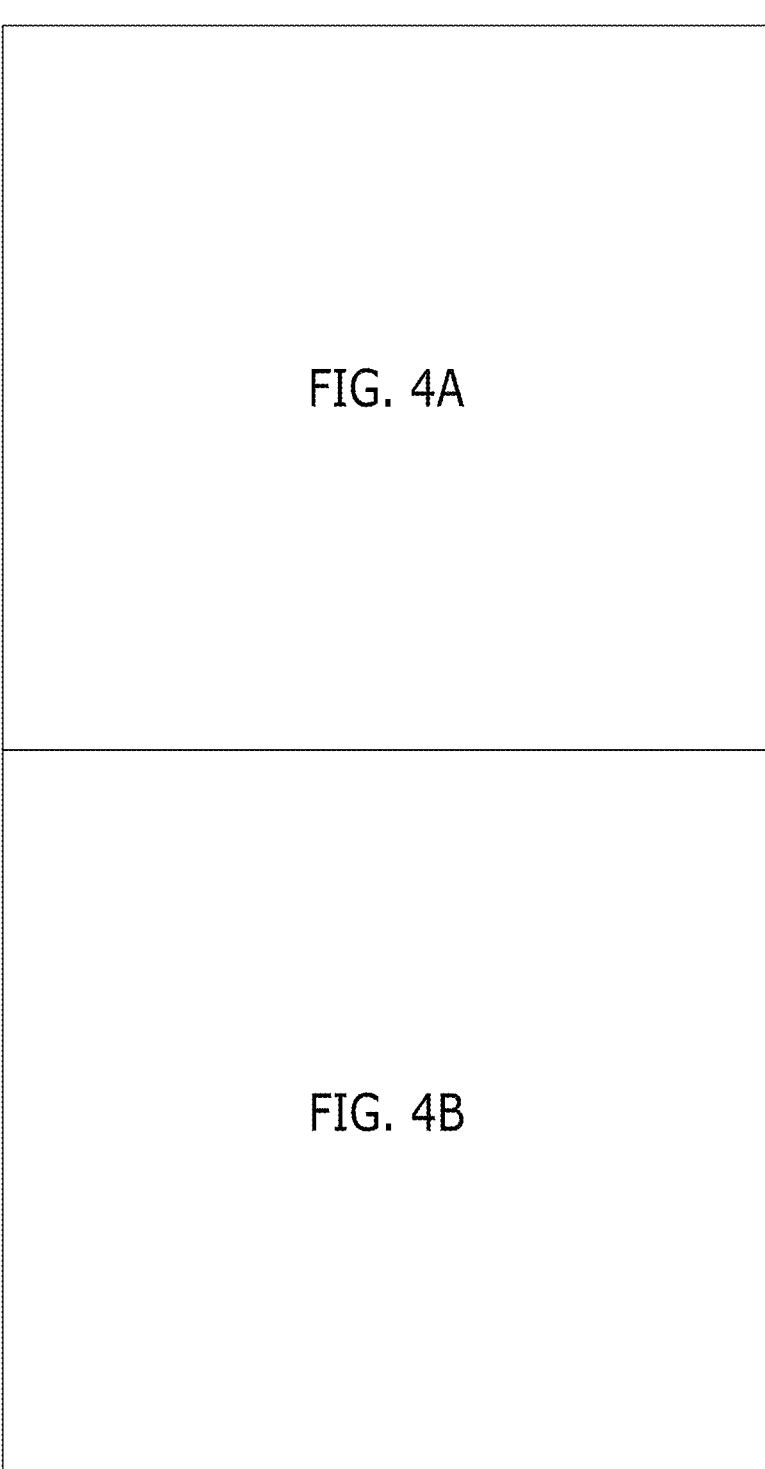
FIG. 4 with partial views FIG. 4A
FIG. 4B illustrates schematically a controller of the water-recycling personal care device of FIGS. 1-3 and a controller of the external device of FIG. 1. The approximate relationship between the partial views is provided by FIG. 4 and alignment guides on the individual partial views allow for alignment of the partial views given the guidance from FIG. 4.
Figure 4A:
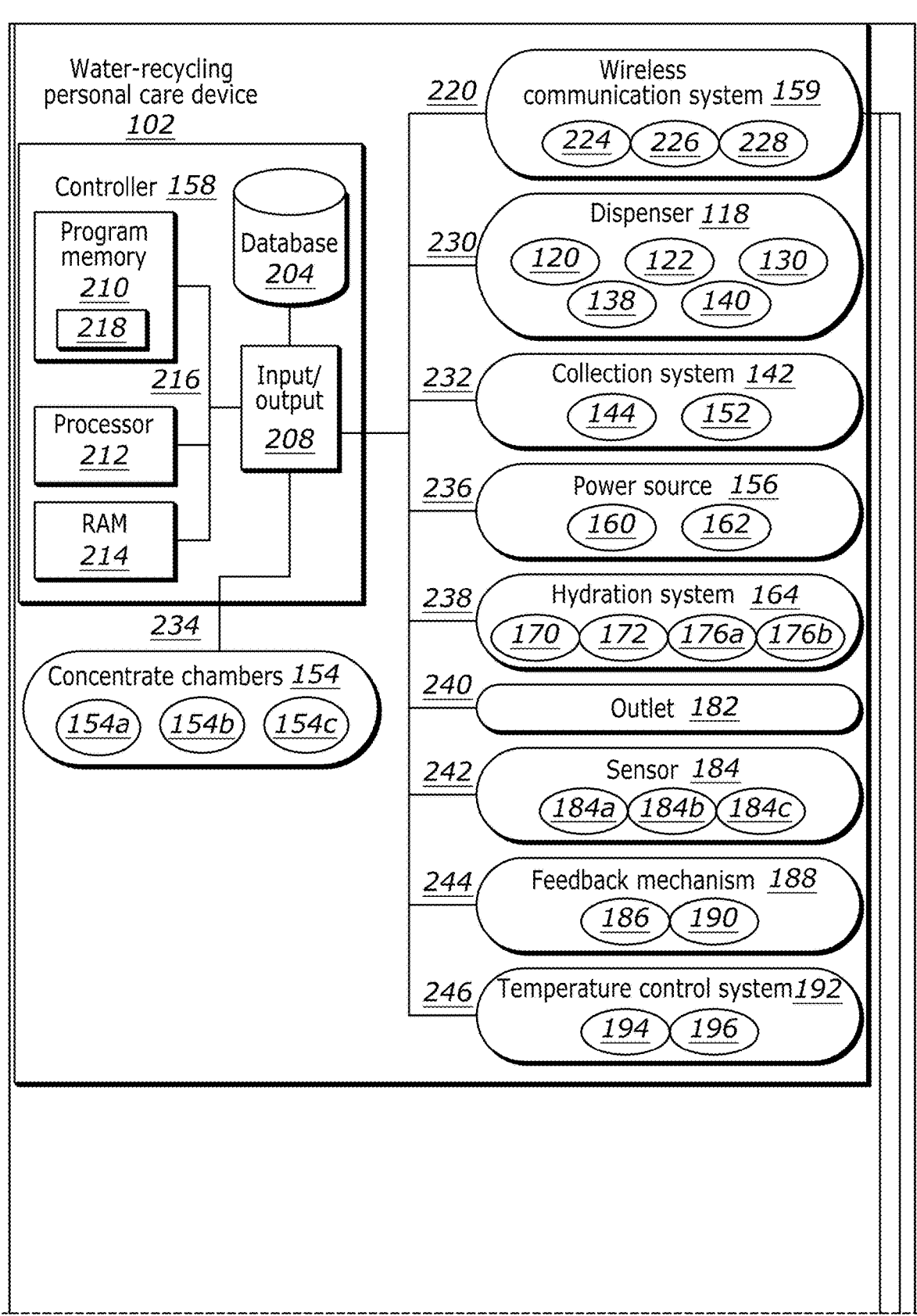
Figure 4B:
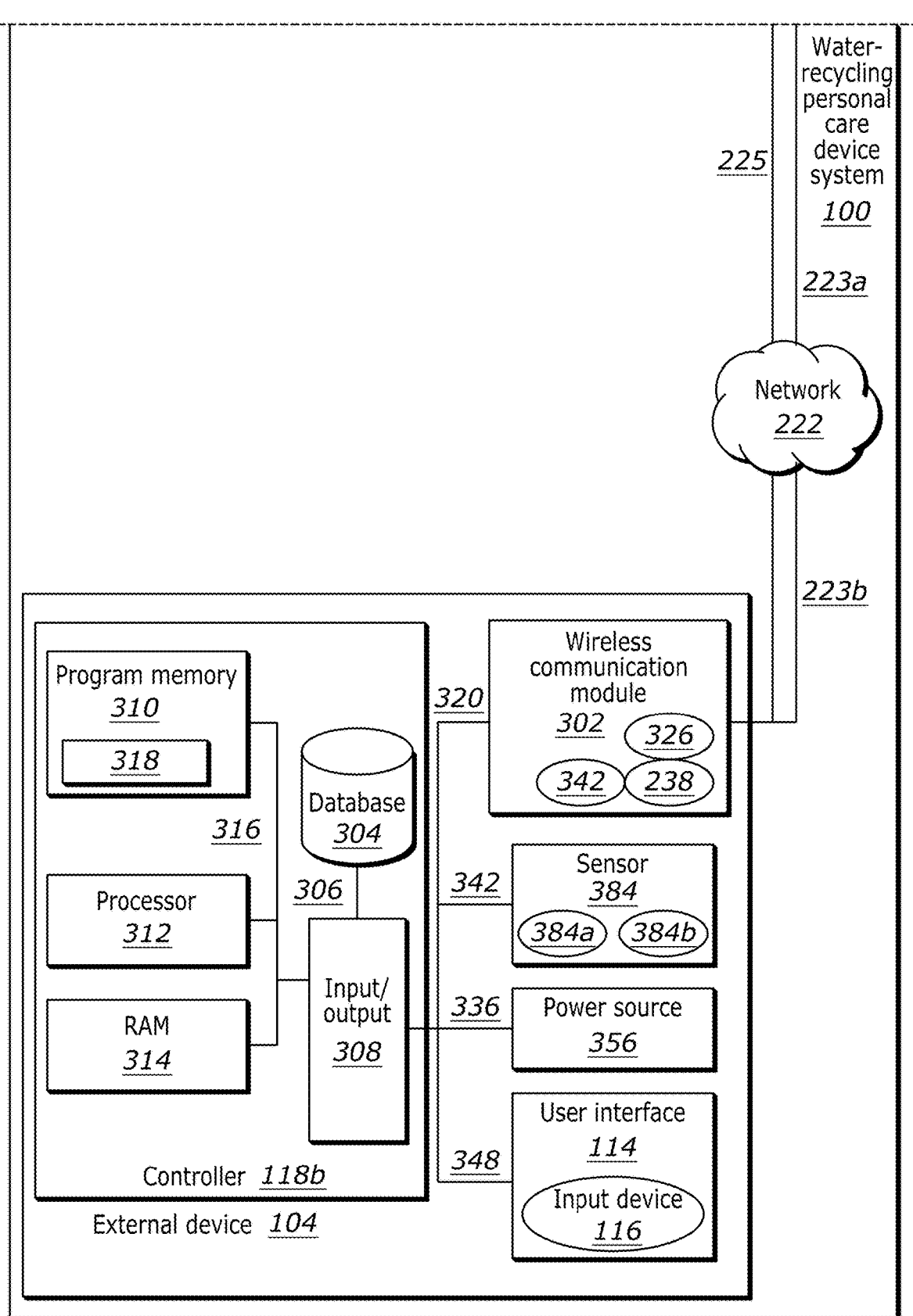

Partial views FIG. 4A and FIG. 4B, aligned as provided in FIG. 4, illustrate schematically the personal care controller 158 of the water-recycling personal care device 102 and the device controller 200 of the external device 104. The personal care controller 158 and the device controller 200, separately or together, are configured to executed the functions of the disclosed arrangements in order to control operation of the water-recycling personal care device 102. The personal care controller 158 and the device controller 300 are in communication via the personal care wireless communication system 159 and the device wireless communication system 302.

The personal care controller 158 may be operatively connected to a database 204 via a link 206 connected to an input/output (I/O) circuit 208. The database 204 may store, for example, various formulations for the cleaning agent 110 from concentrates in concentrate chambers 154, types of audible signals or voice announcements for speaker 190, sensor data collected from one or more sensors 184, diagnostic and usage analytics, including a history of skin metrics, or optimal vacuum levels for vacuum pumps 120 or 144 correlated to quantity of cleaning agent 110 to be or already dispensed. It should be noted that, while not shown, additional databases may be linked to the personal care controller 158 in a known manner. The personal care controller 158 includes a program memory 210 (e.g., a non-transitory memory), one or more processors 212 (may be called microcontrollers or a microprocessors), a random-access memory (RAM) 214, and the input/output (I/O) circuit 208, all of which are interconnected via an address/data bus 216. It should be appreciated that although only one processor 212 is shown, the personal care controller 158 may include multiple microprocessors 212. Similarly, the personal care controller 158 may include multiple RAMs 214 and multiple program memories 210 Although the I/O circuit 208 is shown as a single block, it should be appreciated that the I/O circuit 208 may include a number of different types of I/O circuits. The RAM(s) 214 and the program memories 210 may be implemented as semiconductor memories, magnetically readable memories, and/or optically readable memories, for example.

A link 220, which may include one or more wired and/or wireless (Bluetooth, WLAN, etc.) connections, may operatively connect the personal care controller 158 to the personal care wireless communication system 159 through the I/O circuit 208. The personal care wireless communication system 159 may communicate with the device wireless communication system 302 of the external device 104 (e.g., a smartphone) via respective links 223a and 223b to a network 222 or directly via a link 225. The wireless communication system 159 includes at least one of a Bluetooth chip 224, an NFC chip 226, and an RFID chip 228.

A link 230, which may include one or more wired and/or wireless (Bluetooth, WLAN, etc.) connections, may operatively connect the personal care controller 158 to the dispenser 118. In particular, the link 230 may connect the personal care controller 158 to the vacuum pump 120, actuation button 122, seal 130, aerator 138, and lock 140. In this way, the personal care controller 158 may be used to dispense the cleaning agent 110 and adjust the cleaning agent 110 for dispensing.

A link 232, which may include one or more wired and/or wireless (Bluetooth, WLAN, etc.) connections, may operatively connect the personal care controller 158 to the collection system 142. In particular, the link 232 may connect the personal care controller 158 to the vacuum pump 144 and the oxidizing mechanism 152. In this way, the personal care controller 158 may be used to collect dispensed cleaning agent 110 and water from hydration system 164.

A link 234, which may include one or more wired and/or wireless (Bluetooth, WLAN, etc.) connections, may operatively connect the personal care controller 158 to the concentrate chambers 154 (e.g., 154a, 154b, and 154c). In this way, the personal care controller 158 can be used to release and stop release of concentrates from the concentrate chambers 154 and thereby adjust the formulation of the cleaning agent 110.

A link 236, which may include one or more wired and/or wireless (Bluetooth, WLAN, etc.) connections, may operatively connect the personal care controller 158 to the power source 156. Further, the link 236 may connect the personal care controller 158 to the solar panel array 160 and the kinetic energy harvester 162). In this way, the personal care controller 158 may control the charging and direction of power through the water-recycling personal care device 102.

A link 238, which may include one or more wired and/or wireless (Bluetooth, WLAN, etc.) connections, may operatively connect the personal care controller 158 to the hydration system 164. Specifically, the link 238 may operatively connect the personal care controller 158 to the hydration pump 170, the dehumidifier 172, the valve 176*a*, and the valve 176*b*). In this way, the personal care controller 158 may control dispensing of water through the hydration system 164.

A link 240, which may include one or more wired and/or wireless (Bluetooth, WLAN, etc.) connections, may operatively connect the personal care controller 158 to the outlet 182 for a secondary attachment 180. In this way, the personal care controller 158 may provide power to and receive sensor data from secondary attachments 180, such as medicated heads or light treatment systems.

A link 242, which may include one or more wired and/or wireless (Bluetooth, WLAN, etc.) connections, may operatively connect the personal care controller 158 to a sensor 184, or a plurality of sensors (184*a*, 184*b*, 184*c* . . . ). For example, the link 242 may be connected to a pressure sensor 184*a*, a light sensor 184*b*, a humidity sensor 184*c*, and any other sensors 184 provided in or on the water-recycling personal care device 102.

A link 244, which may include one or more wired and/or wireless (Bluetooth, WLAN, etc.) connections, may operatively connect the personal care controller 158 to the feedback mechanism 188. Specifically, the link 244 may connect the personal care controller 158 to lights 186 and speaker 190. The feedback mechanism 244 may further include the user interface 114 of the external device 104, which accessible by the personal care controller 158 or the device controller 300 via the personal care wireless communication system 159, network 222, and device wireless communication system 303. The feedback mechanism 188 provides a user with relevant information via visual, auditory, haptic notices.

A link 246, which may include one or more wired and/or wireless (Bluetooth, WLAN, etc.) connections, may operatively connect the personal care controller 158 to the temperature control system 192. Specifically, the link 246 may connect the personal care controller 158 to the fan 194 and the heater 196. In some cases, one of the sensors 184 may be a temperature sensor, and the personal care controller 158 may control the temperature control system 192 to maintain a desired temperature.

Other links are contemplated as within the scope of this disclosure.

The program memory 210 and/or the RAM 214 may store various applications (i.e., machine readable instructions) for execution by the processor 212. The program memory 210 and/or the RAM 214 may also store a variety of subroutines 218 for accessing specific functions of the personal care controller 158. By way of example, and without limitation, the subroutines 218 may include, among other things:

a subroutine 218 for causing the personal care controller 158 to adjust a quality or amount of the quantity of cleaning agent 110 dispensed from the dispenser 118, whereby adjusting the quality or amount of the quantity of cleaning agent 110 includes, for example, changing a predetermined amount of the quantity of cleaning agent, changing a formulation of the quantity of cleaning agent, changing a temperature of the quantity of cleaning agent, or any other adjustment to the cleaning agent 110 being dispensed from the water-recycling personal care device 102;

a subroutine 218 for adjusting the quality or amount of the quantity of cleaning agent 110 dispensed from the dispenser 118 in response to user input provided at the input device 116;

a subroutine 218 for causing the speaker 190 to produce an audible signal, such as a voice announcements;

a subroutine 218 for adjusting operation of the water-recycling personal care device 102 in response to sensor data;

a subroutine 218 for adjusting operation of the water-recycling personal care device 102 in response to the sensor data including at least one of changing the quantity of the cleaning agent 110 dispensed from the dispenser 118, changing a vibration of the water-recycling personal care device 102, changing a formulation of the cleaning agent 110, and changing a vacuum level of the collection system 142;

a subroutine 218 for changing the vibration of the water-recycling personal care device 102 that includes at least one of turning on the motor, turning off the motor, and adjusting a speed of the motor;

a subroutine 218 for changing a formulation of the cleaning agent 110 that includes fluidly connecting at least one of the plurality of concentrate chambers 154 to the reservoir 108 to add the respective concentrate of each of the at least one of the plurality of concentrate chambers to the cleaning agent 110;

a subroutine 218 for changing a vacuum level of the collection system 142 that includes adjusting the vacuum level generated by the vacuum pump 144;

a subroutine 218 for storing sensor data as stored sensor data;

a subroutine 218 for analyzing the stored sensor data and providing personal care recommendations;

a subroutine 218 for identifying usage and providing details on frequencies or times of use, e.g. via the stored sensor data;

a subroutine 218 for providing previous personal care recommendations based on the stored sensor data;

a subroutine 218 for identifying changes in skin metrics such as moisture or clarity using, e.g., the stored sensor data;

a subroutine 218 for communicating, via the device wireless communication 202 and personal care wireless communication system 159, the personal care recommendations to the device controller 200;

a subroutine 218 for the personal care recommendations that includes at least one of recommending an attachment for the water-recycling personal care device 102, recommending an adjustment to the quality or amount of the quantity of cleaning agent 110 dispensed, recommending an adjustment to a formulation of the cleaning agent 110 dispensed, recommending an application technique, and recommending an application time;

a subroutine 218 for adjusting operation of the water-recycling personal care device 102 in response to the selected one or more of the input options;

a subroutine 218 for adjusting the operation of the water-recycling personal care device 102 in response to the selected one or more of the input options that includes facilitating replacement of the pad 112 with an attachment, adjusting the quality or amount of the quantity of cleaning agent 110 dispensed, and adjusting a formulation of the cleaning agent 110 dispensed;

a subroutine 218 for activating the feedback mechanism 188 when a threshold setting has been met;

a subroutine 218 for activating the feedback mechanism 188 when a threshold setting has been met wherein the threshold setting is one of a period of time expiring and sensor data exceeding a preset sensor threshold;

a subroutine 218 that at least one of turns on, turns off, or changes a color of the light 186 in response to a component status; and a subroutine 218 that at least one of turns on, turns off, or changes a color of the light 186 in response to a component status where the component status is one of a use time of the pad 112, a fill level of the reservoir 108, a level of power of the power source 156, and a filter efficacy of the collection system 142.

The external device 104, and device controller 300, include any or all of the components common to smart-phones with select components identified below. The device controller 300 may be operatively connected to a database 304 via a link 306 connected to an input/output (I/O) circuit 308. Like database 204, the database 304 may store, for example, various formulations for the cleaning agent 110 from concentrates in concentrate chambers 154, types of audible signals or voice announcements for speaker 190, sensor data collected from one or more sensors 184, or optimal vacuum levels for vacuum pumps 120 or 144 correlated to quantity of cleaning agent 110 to be or already dispensed. The controller 300 includes a program memory 310, one or more processors 312 (may be called microcontrollers or a microprocessors), a random-access memory (RAM) 314, and the input/output (I/O) circuit 308, all of which are interconnected via an address/data bus 316. It should be appreciated that although only one processor 312 is shown, the device controller may include multiple microprocessors 312. Similarly, the device controller 300 may include multiple RAMs 314 and multiple program memories 310 Although the I/O circuit is shown as a single block, it should be appreciated that the I/O circuit 308 may include a number of different types of I/O circuits. The RAM(s) 314 and the program memories 310 may be implemented as semiconductor memories, magnetically readable memories, and/or optically readable memories, for example.

A link 348, which may include one or more wired and/or wireless (Bluetooth, WLAN, etc.) connections, may operatively connect the device controller 300 to the user interface 114, which may include the input device 116, through the I/O circuit 308. A link 320, which may include one or more wired and/or wireless (Bluetooth, WLAN, etc.) connections, operatively connects the device controller 300 to the device wireless communication system 302. As described above, the device wireless communication system 302 may communicate with the personal care wireless communication system 159 via respective links 223*a* and 223*b* and network 222 or directly via link 225. The device wireless communication system 302 includes at least one of a Bluetooth chip 324, an NFC chip 326, and an RFID chip 328. Further, one or more sensors 384 (e.g., 384*a*, 384*b*) to collect sensor data is operatively connected to the device controller 200 through the I/O circuit 308 by a link 342. A power source 356 is connected to the device controller 300 by a link 336. Other links are contemplated as within the scope of this disclosure.

The program memory 310 and/or the RAM 314 may store various applications (i.e., machine readable instructions) for execution by the processor 312. The program memory 310 and/or the RAM 314 may also store a variety of subroutines 318 for accessing specific functions of the device controller 300. By way of example, and without limitation, the subroutines 318 may include, among other things:

a subroutine 318 for sending, via the device wireless communication 202 and personal care wireless communication system 159, user input provided at the input device 116 relating to, for example, how the quantity of agent dispensed from the dispenser 118 should be adjusted;

a subroutine 318 for receiving, via the device wireless communication 202 and personal care wireless communication system 159, sensor data and store the sensor data as stored sensor data;

a subroutine 318 for analyzing the stored sensor data and provides personal care recommendations;

a subroutine 318 for displaying the personal care recommendations on the user interface 114;

a subroutine 318 for displaying input options on the user interface 114, soliciting selection of one or more of the input options by the input device 116, and communicating the selected one or more of the input options to the personal care controller 158 via the device wireless communication 202 and personal care wireless communication system 159;

a subroutine 318 for activating the feedback mechanism 188 when a threshold setting has been met; and a subroutine 318 for activating the feedback mechanism 188 when a threshold setting has been met, wherein the threshold setting is one of a period of time expiring and sensor data exceeding a preset sensor threshold.

Figure 5:
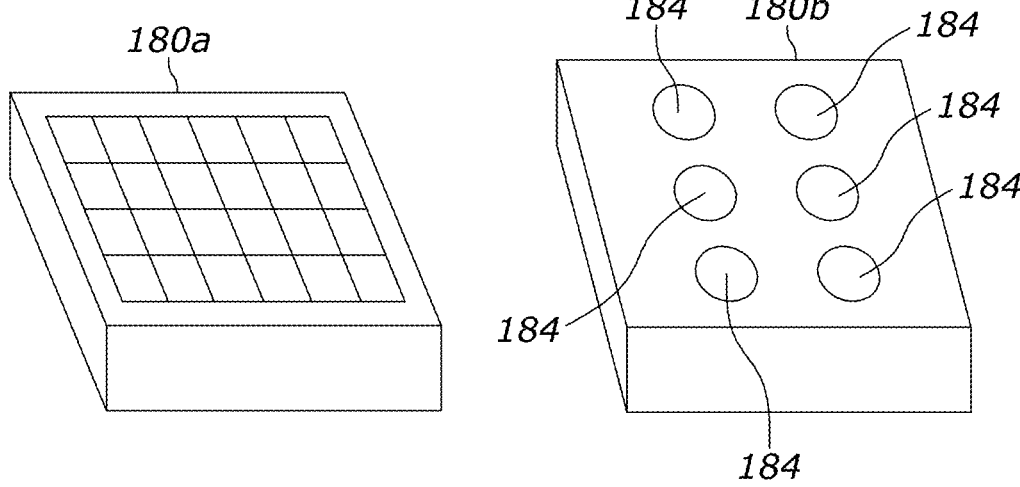
FIG. 5 illustrates a perspective view of a pad and secondary attachment for the personal care device of FIGS. 1-3.
Figure 5:
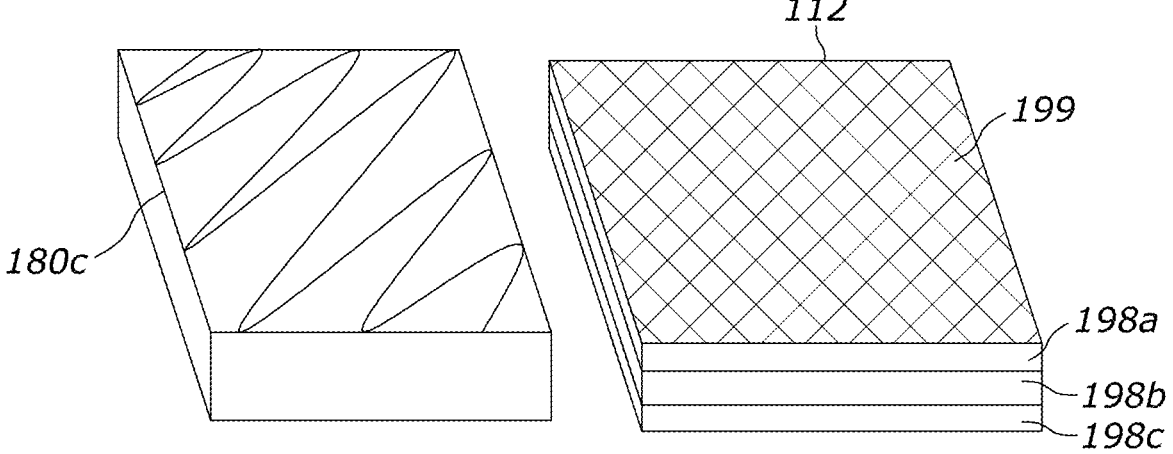

Turning to FIG. 5, the pad 112 of the water-recycling personal care device 102 includes a plurality of layers 198. Specifically, the pad 112 is shown with three layers: 198*a*, 198*b*, and 198*c*. In other arrangements, the pad 112 may have fewer or more layers 198. In the arrangement shown, the first layer 198*a* includes an exfoliating surface 199. The second layer 198*b* includes an antimicrobial material to prevent bacterial buildup in the pad 112. The third layer 198*c* includes the absorbent material 124 to enable collection of the cleaning agent 110 after use.

FIG. 5 also depicts three secondary attachments 180 (180*a*, 180*b*, and 180*c*). The secondary attachment 180*a* is an LED light treatment head. For example, the LED light treatment head may include LED lights configured to emit red light to treat scars, wrinkles, or redness. As another example, the LED light treatment head may include LED lights configured to emit blue light to treat acne. The secondary attachment 180*b* is a diagnostic tool including sensors 184. The diagnostic tool 180*b* may, for example, determine environmental conditions or skin conditions by sensing temperature, humidity, moisture, or by collecting visual data that can be analyzed to assess skin quality. The secondary attachment 180*c* is a specialized treatment head for, for example, acne or deep hydration. An ointment, astringent, cream, medication, or the like may be provided on the secondary attachment 180*c* to be applied to a user's face. For example, a retinol treatment may be placed on the secondary attachment 180*c* and spread on a user's face. The secondary attachment 180*c* includes a textured surface to keep treatments from running off the secondary attachment 180*c*. The secondary attachments 180 are interchangeable with the pad 112 and removably attach to the housing 106. The secondary attachments 180 may connect to the power source 156 and the personal care controller 158, as well as other features of the water-recycling personal care device 102, via the outlet 182. Although all secondary attachments 180*a*, 180*b*, and 180*c* are shown having substantially the same size and shape, other sizes and shapes are possible.

Figure 6:
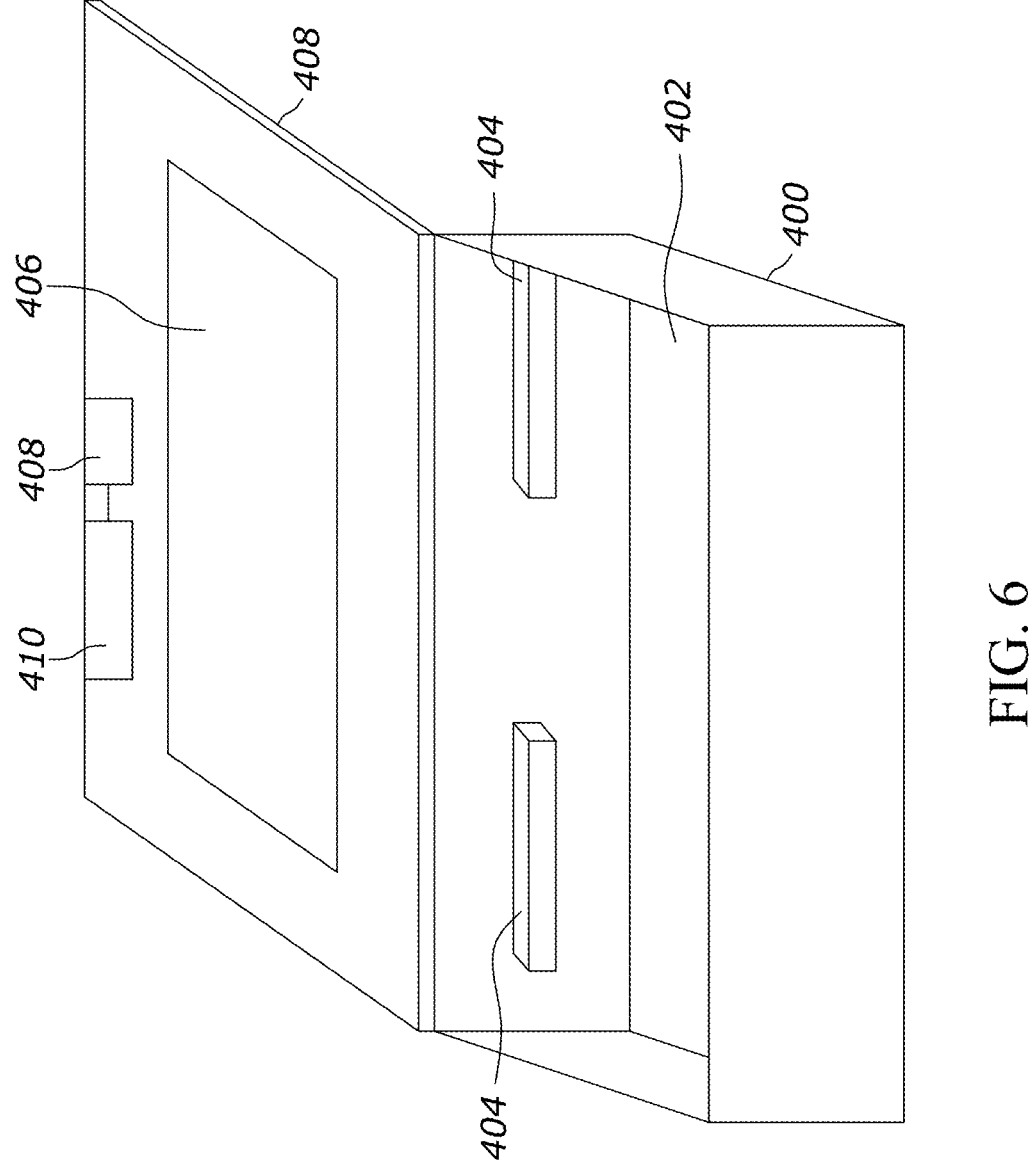
FIG. 6 illustrates a perspective view of a case for storing the personal care device of FIGS. 1-3.

FIG. 6 illustrates a case 400 for the water-recycling personal care device 102. The case 400 includes a receptacle 402 for storing the water-recycling personal care device 102. The receptacle 402 may, for example, have a complementary shape to the water-recycling personal care device 102 or may include grips 404 to secure the water-recycling personal care device 102 in place. The receptacle 402 may further include a UV light 406 to sanitize the water-recycling personal care device 102. In some arrangements, the case 400 may include a lid 408 and the UV light 406 may be provided on an interior side of the lid. The UV light 406 may be connected to a power source 410 and a pressure sensor positioned on the lid 408 to sense when the lid 408 is closed. When the pressure at the pressure sensor 412 indicates that the lid 408 is closed, the UV light 406 may turn on. When the pressure at the pressure sensor 414 indicates that the lid is open, the UV light 406 may turn off.

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" or "some embodiments" means that a particular element, feature, structure, or characteristic described in connection with the embodiment is included in at least one embodiment. The appearances of the phrase "in one embodiment" or "in some embodiments" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for cosmetic application, and/or systems, methods, and/or techniques associated therewith. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A water-recycling personal care device comprising:
   a housing having a reservoir, the reservoir configured to contain a cleaning agent;
   a pad removably connected to the housing;
   a dispenser contained within the housing and configured to dispense a quantity of the cleaning agent from the reservoir; and
   a collection system configured to collect the quantity of the cleaning agent dispensed from the reservoir after use,
   wherein the pad comprises an absorbent material to absorb the quantity of the cleaning agent,
   wherein the collection system includes a vacuum pump in fluid communication with the absorbent material of the pad, and
   wherein the collection system includes a filter chamber into which the quantity of the cleaning agent is pumped by the vacuum pump, the filter chamber including a filter to remove debris from the quantity of the cleaning agent, and wherein the filter chamber is in fluid communication with the reservoir, and the quantity of the cleaning agent is returned to the reservoir after passing through the filter.

2. The water-recycling personal care device of claim 1 further comprising an oxidizing mechanism configured to oxidize the debris.

3. The water-recycling personal care device of claim 1 further comprising a power source contained within the housing and a controller comprising a non-transitory memory and one or more processors, the controller in electrical communication with the power source.

4. The water-recycling personal care device of claim 3 further comprising a solar panel array in electrical communication with the power source.

5. The water-recycling personal care device of claim 3 further comprising a kinetic energy harvester in electrical communication with the power source.

6. The water-recycling personal care device of claim 3 further comprising a sensor in communication with the controller, the sensor configured to collect sensor data.

7. The water-recycling personal care device of claim 6, wherein the sensor is one of a temperature sensor, a humidity sensor, an air quality sensor, a biometric sensor, and a pressure sensor.

8. The water-recycling personal care device of claim 3 further comprising a feedback mechanism in communication with the controller, the feedback mechanism configured to provide at least one of visual feedback, olfactory feedback, auditory feedback, and haptic feedback.

9. The water-recycling personal care device of claim 1 further comprising a motor within the housing, the motor configured to vibrate the pad.

10. The water-recycling personal care device of claim 1 further comprising a secondary attachment configured to removably attach to the housing and interchangeable with the pad.

11. The water-recycling personal care device of claim 10, wherein the secondary attachment is at least one of a replacement microfiber pad, an acne treatment head, a diagnostic head, and an LED light head.

12. The water-recycling personal care device of claim 1 further comprising a hydration system including a water cavity positioned within the housing, a nozzle connected to the housing, and a pump configured to pump water between the water cavity and the nozzle.

13. The water-recycling personal care device of claim 1, the dispenser including a lock to prevent accidental dispensing during periods of non-use or under conditions of altered gravity.

14. The water-recycling personal care device of claim 1 further comprising a temperature control system.

15. The water-recycling personal care device of claim 1, wherein the reservoir is configured to fluidly connect to a plurality of concentrate chambers, each concentrate chamber containing a respective concentrate suitable for use in the cleaning agent.

16. A water-recycling personal care device comprising:
    a housing having a reservoir, the reservoir configured to contain a cleaning agent;
    a pad removably connected to the housing;
    a dispenser contained within the housing and configured to dispense a quantity of the cleaning agent from the reservoir; and
    a collection system configured to collect the quantity of the cleaning agent dispensed from the reservoir after use,
wherein the dispenser includes an aerator, and the cleaning agent is a foaming cleaning agent that foams in response to aeration by the aerator.

17. A water-recycling personal care device comprising:
a housing having a reservoir, the reservoir configured to contain a cleaning agent;
    a pad removably connected to the housing;
    a dispenser contained within the housing and configured to dispense a quantity of the cleaning agent from the reservoir; and
    a collection system configured to collect the quantity of the cleaning agent dispensed from the reservoir after use, and
further comprising a dehumidifier configured to collect water from an environment outside the housing and direct the water to the reservoir.

* * * * *